US00PP26339P3

(12) United States Plant Patent
Egger

(10) Patent No.: US PP26,339 P3
(45) Date of Patent: Jan. 19, 2016

(54) *HEUCHERA* PLANT NAMED 'GRAPE SODA'

(50) Latin Name: ***Heuchera* hybrid**
Varietal Denomination: Grape Soda

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 150 days.

(21) Appl. No.: 13/999,447

(22) Filed: Feb. 25, 2014

(65) Prior Publication Data

US 2015/0245552 P1 Aug. 27, 2015

(51) Int. Cl.
*A01H 5/02* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by leaves which are colored rose to light plum, strongly veiled, and medium large, warm pink flowers on dark peduncles, great winter foliage color, a medium, mounding habit, excellent tolerance to heat and humidity, and excellent vigor.

2 Drawing Sheets

Botanical denomination: *Heuchera* hybrid.
Variety designation: 'Grape Soda'.

BACKGROUND OF THE INVENTION

The present invention relates to a new and distinct cultivar of *Heuchera* and given the cultivar name of 'Grape Soda'. *Heuchera* is in the family Saxifragaceae. *Heuchera* 'Grape Soda' originated as a controlled cross using *Heuchera* K494-7, a proprietary, unnamed plant as the seed parent, and *Heuchera* 'Georgia Plum' U.S. Plant Pat. No. 24,507, as the pollen parent.

Compared to the pollen parent and only similar cultivar, *Heuchera* 'Georgia Plum', the new cultivar is slightly larger, faster growing, with more crowns and shorter petioles. The foliage is slightly less purple and the flowers are pinker.

Compared to the seed parent K494-7, the new cultivar has rose to plum leaves rather than silver.

Compared to *Heuchera* 'Plum Royal', U.S. Plant Pat. No. 20,935, the new cultivar has rose to plum colored leaves rather than plum to silver and warm pink flowers rather than pink to white flowers.

This new *Heuchera* is uniquely distinguished by:

1. leaves which are colored rose to light plum, strongly veiled, and medium large,
2. warm pink flowers on dark peduncles,
3. great winter foliage color,
4. a high crown count and fast growth that fill the pots quickly,
5. a medium, mounding habit,
6. excellent tolerance to heat and humidity,
7. and excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a nine-month-old plant of *Heuchera* 'Grape Soda' growing in a one gallon container, grown in a cool greenhouse in April in Canby, Oreg.

FIG. 2 shows a two-year-old plant growing in the trial beds in April in Canby, Oreg.

FIG. 3 shows a two-year-old in a one gallon container in June.

FIG. 4 shows a one and one-half-year-old plant in February in the trial beds in Canby, Oreg.

DETAILED PLANT DESCRIPTION

The following is a detailed description of the new *Heuchera* cultivar based on observations taken in late June of one and one-half-year-old specimens growing in one gallon containers, grown outside in a shade house in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—21 cm tall from top of the foliage to the ground and 45 cm wide.
*Habit.*—Mounding.
*Vigor.*—Good.

Leaf:

*Type.*—Simple.

*Arrangement.*—Rosette.

*Shape.*—Broadly ovate to orbicular.

*Lobing/division.*—5 to 7 shallow lobes, the terminal the longest, shallow secondary lobes.

*Venation.*—Palmate.

*Margins.*—Crenate, with no undulations.

*Apex.*—Mucronulate.

*Base.*—Cordate, lobes overlapping slightly at the base.

*Blade size.*—Grows to 13 cm long and 12 cm wide.

*Surface texture.*—Glandular on both sides, surface semi-glossy.

*Petiole description.*—Grows to 17 cm long and 2.5 mm wide, glandular hairs, Greyed Purple 187B.

*Rugosity.*—Absent.

*Leaf color.*—Variable depending on season and age of the leaf, veins with strong colors and between the veins (interveinally) there is a heavy "silver" veil lightening the leaf color; topside, spring new leaves between Greyed Purple 185A and Red Purple 62A with the edges and veins Greyed Purple 187B, bottom side closest to Red Purple 59B all over; topside summer, fall Purple N77C with the edges and veins N77A, bottom side closest to Red Purple N79B all over; winter color same as summer but slightly more silver.

Inflorescence:

*Size.*—Grows to 6 cm wide and 17 cm long.

*Type.*—Thyrse.

*Number of flowers per thyrse.*—About 80.

*Number of thyrse.*—About 10 in first spring flush.

*Peduncle.*—Grows to 24 cm long and 3 mm wide at base, Greyed Purple 187A, glandular hairs.

*Pedicel.*—Variable in size, with glandular hairs, Greyed Purple 187A.

*Attitude.*—Upright.

*Bloom period.*—Heavy June bloom then occasional blooms May through October in Canby, Oreg.

Flower bud:

*Size.*—2.5 mm wide and 5 mm long.

*Description.*—Glandular puberulent, ovoid, down facing.

*Color.*—Red Purple 59C.

Flower:

*Type.*—Perfect.

*Shape.*—Campanulate.

*Size.*—7 mm long and 5.5 mm wide.

*Attitude.*—Outwards to semi-downwards.

*Corolla description.*—5 petals, 3 mm long and less than 1 mm wide, recurved, spatulate, margins entire, tip acute, glabrous on topside and bottom side, Red Purple 65C on both sides.

*Calyx description.*—Campanulate, 7 mm long and 6 mm wide, with 5 lobes divided ½ way to the base, each 2 mm wide and 2.5 mm long, glandular on top and bottom, tip obtuse, margin entire; color both sides Red Purple 70B with lobe edges 70D.

*Stamen description.*—5 in number, filaments 2 mm long, White N155B, anthers 0.4 mm, Orange 26A, pollen Orange 25A.

*Pistil description.*—1, 2-beaked, 6 mm long and 1.8 mm wide, Red Purple 69A overall, ovary 2 mm long and 1.8 mm wide, style 4 mm long.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

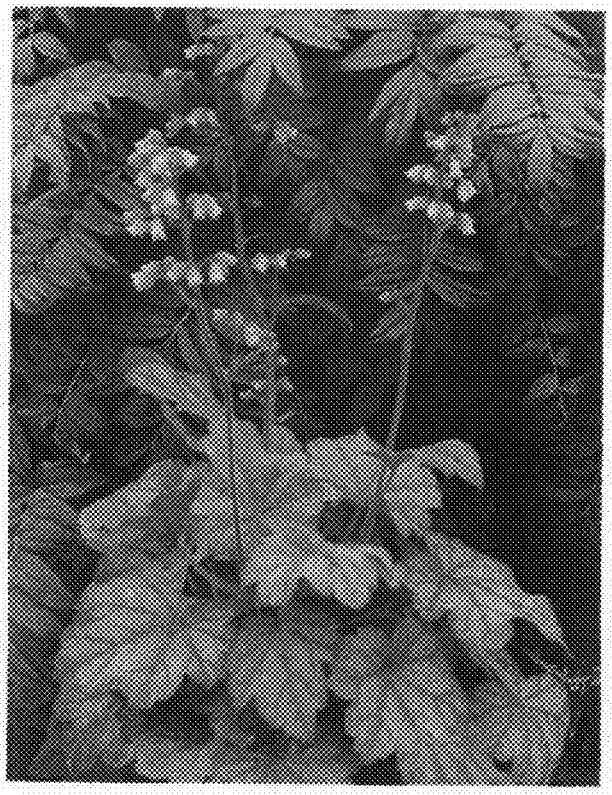
FIG. 1 above, FIG. 2 below
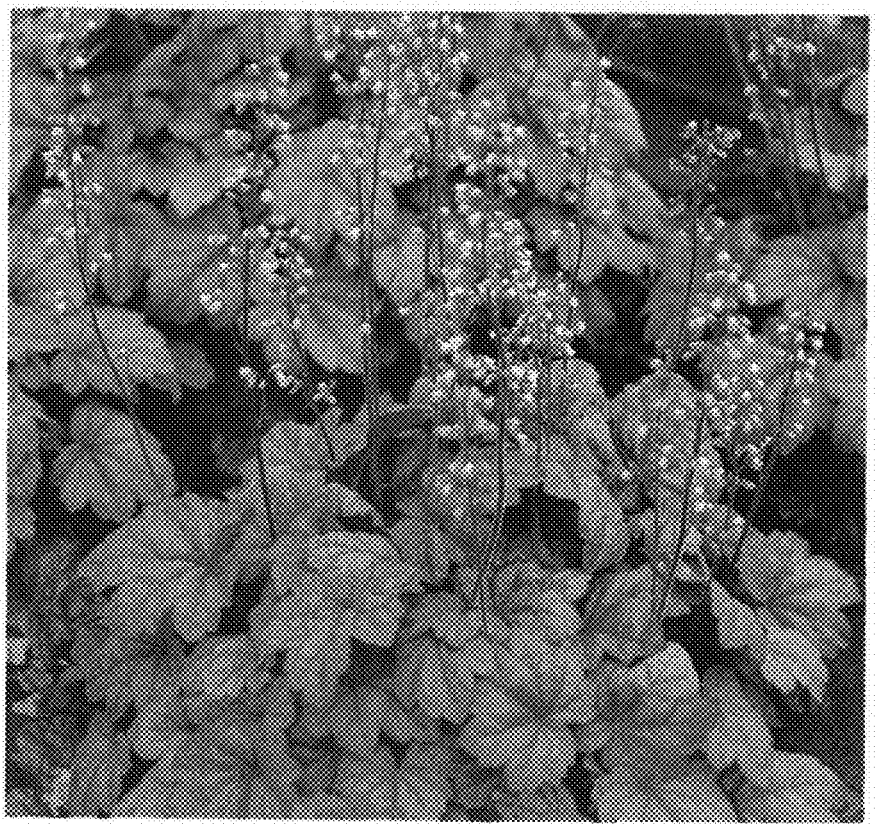

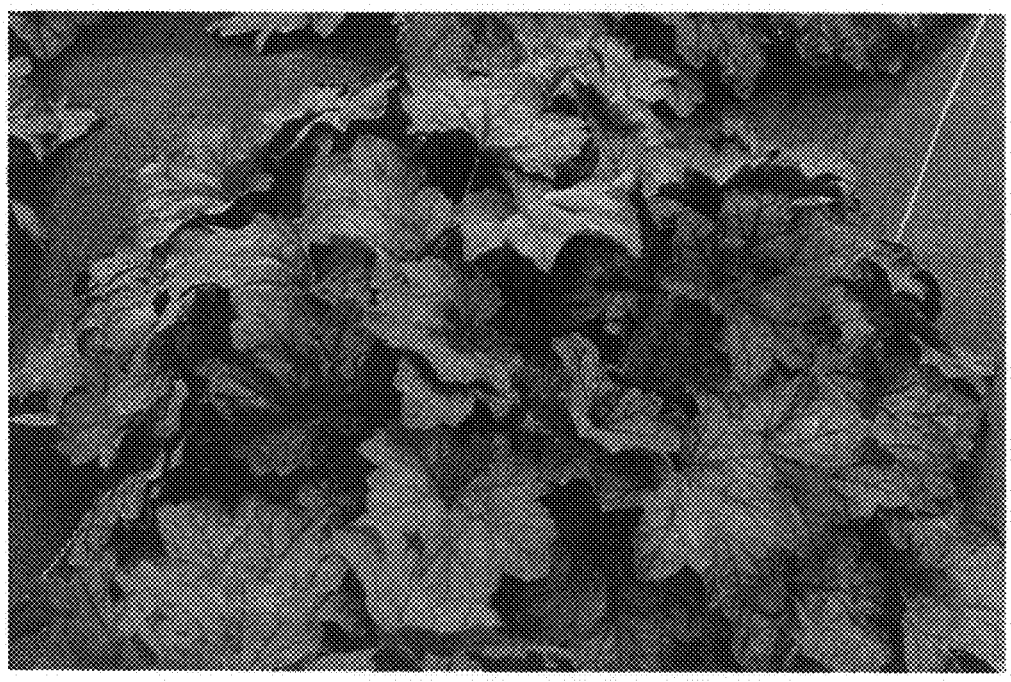

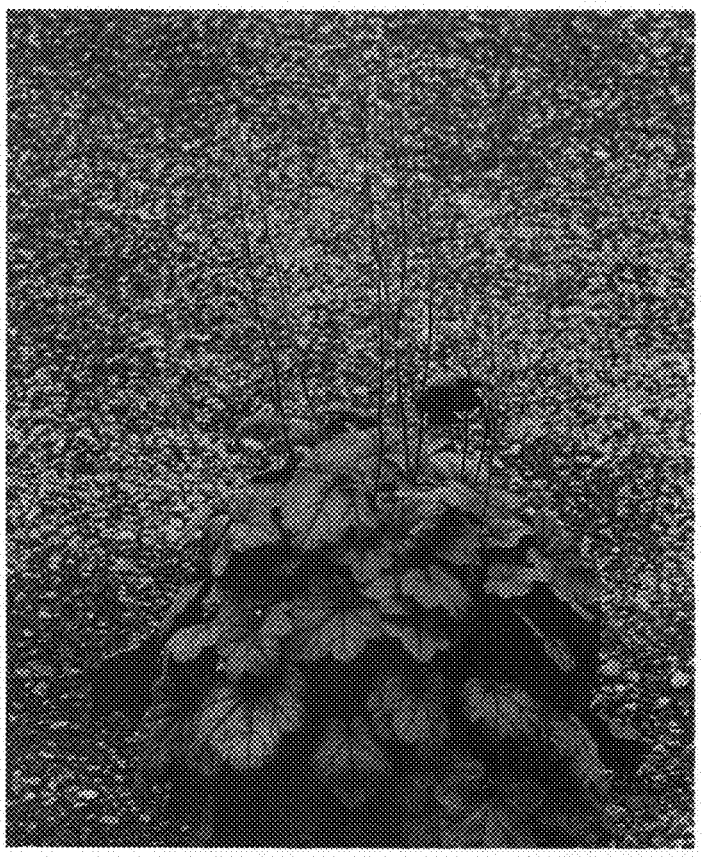
FIG. 3 above, FIG. 4 below